(12) United States Patent
Kuboi et al.

(10) Patent No.: US 10,064,542 B2
(45) Date of Patent: Sep. 4, 2018

(54) BENDING APPARATUS WITH BENDING DIRECTION RESTRICTION MECHANISM

(71) Applicant: OLYMPUS CORPORATION, Tokyo (JP)

(72) Inventors: Toru Kuboi, Hachioji (JP); Ryo Tojo, Hachioji (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 304 days.

(21) Appl. No.: 14/818,843

(22) Filed: Aug. 5, 2015

(65) Prior Publication Data

US 2015/0335226 A1 Nov. 26, 2015

Related U.S. Application Data

(63) Continuation of application No. PCT/JP2014/051625, filed on Jan. 27, 2014.

(30) Foreign Application Priority Data

Feb. 6, 2013 (JP) .................................. 2013-021246

(51) Int. Cl.
*A61B 1/005* (2006.01)
*A61B 1/00* (2006.01)
(Continued)

(52) U.S. Cl.
CPC ........ *A61B 1/0051* (2013.01); *A61B 1/00112* (2013.01); *A61B 1/00131* (2013.01);
(Continued)

(58) Field of Classification Search
CPC .............. A61B 1/0051; A61B 1/00112; A61B 1/00131; A61B 1/00165; A61B 1/07;
(Continued)

(56) References Cited

U.S. PATENT DOCUMENTS 5,633,494 A * 5/1997 Danisch ............. G02B 6/02057
250/227.14
6,059,718 A * 5/2000 Taniguchi ............ A61B 1/0005
600/117
(Continued)

FOREIGN PATENT DOCUMENTS

JP 2001169998 A * 6/2001 ......... A61B 1/00165
JP 2002-345729 A 12/2002
(Continued)

OTHER PUBLICATIONS

Chinese Office Action dated Mar. 7, 2017 in Chinese Patent Application No. 201480007715.8.
(Continued)

*Primary Examiner* — John P Leubecker
(74) *Attorney, Agent, or Firm* — Scully, Scott, Murphy & Presser, P.C.

(57) ABSTRACT

A bending apparatus includes a shape sensor including a light source, an optical fiber, a detecting part, and a light receiver. The shape sensor utilizes a variation in optical characteristics, which is detected by the detecting part in accordance with a variation of curvature of the optical fiber when the optical fiber is bent. The shape sensor is freely bendable in any direction and having directivity in detection sensitivity for a bending direction. A bending direction restriction mechanism is combined with the shape sensor and has bending directivity including such a property of ease in bending that bending is easy in at least a specific direction other than a direction of a center line, and such a property of difficulty in bending that bending is difficult in directions other than the specific direction.

20 Claims, 7 Drawing Sheets

(51) Int. Cl.
*A61B 1/018* (2006.01)
*G02B 23/24* (2006.01)
*A61B 1/07* (2006.01)
*G02B 23/26* (2006.01)
*A61B 34/20* (2016.01)

(52) U.S. Cl.
CPC .......... *A61B 1/00165* (2013.01); *A61B 1/018* (2013.01); *A61B 1/07* (2013.01); *G02B 23/2476* (2013.01); *A61B 2034/2061* (2016.02); *G02B 23/26* (2013.01)

(58) Field of Classification Search
CPC .......... A61B 1/0055; A61B 2034/2061; G02B 23/2476; G02B 23/26
See application file for complete search history.

(56) References Cited

U.S. PATENT DOCUMENTS

| | | | | |
|---|---|---|---|---|
| 6,471,710 | B1* | 10/2002 | Bucholtz | G01B 11/18 600/229 |
| 2001/0021843 | A1* | 9/2001 | Bosselmann | A61B 34/70 606/2 |
| 2002/0183592 | A1* | 12/2002 | Suzuki | A61B 1/00071 600/145 |
| 2007/0116415 | A1 | 5/2007 | Kobayashi | |
| 2007/0265503 | A1* | 11/2007 | Schlesinger | A61B 5/065 600/182 |
| 2008/0097159 | A1* | 4/2008 | Ishiguro | A61B 1/0051 600/145 |
| 2010/0099951 | A1 | 4/2010 | Laby et al. | |
| 2010/0298844 | A1 | 11/2010 | Blumenkranz | |
| 2011/0098533 | A1* | 4/2011 | Onoda | A61B 1/0051 600/117 |
| 2011/0172519 | A1* | 7/2011 | Cao | A61B 5/06 600/424 |
| 2011/0174108 | A1* | 7/2011 | Graham | A61B 5/065 74/490.05 |
| 2011/0319714 | A1* | 12/2011 | Roelle | A61B 1/00006 600/118 |
| 2011/0319815 | A1* | 12/2011 | Roelle | A61B 1/00149 604/95.01 |
| 2013/0096423 | A1* | 4/2013 | Yamamoto | A61B 1/00006 600/424 |
| 2013/0261392 | A1 | 10/2013 | Yamamoto et al. | |
| 2016/0228199 | A1* | 8/2016 | Flexman | G02B 23/2476 |

FOREIGN PATENT DOCUMENTS

| | | | | |
|---|---|---|---|---|
| JP | 2007-143600 | A | 6/2007 | |
| JP | 4454747 | B2 * | 4/2010 | ......... A61B 1/00165 |
| JP | 2011-104053 | A | 6/2011 | |
| JP | 4714570 | B2 | 6/2011 | |
| JP | 2011-200341 | A | 10/2011 | |
| JP | 2011-217836 | A | 11/2011 | |
| JP | 2012-115521 | A | 6/2012 | |
| WO | 2012/074016 | A1 | 6/2012 | |

OTHER PUBLICATIONS

Extended Supplementary European Search Report dated Aug. 10, 2016 in related European Application No. 14 74 9446.2.
Japanese Office Action dated Aug. 16, 2016 in related Japanese Patent Application No. 2013-021246.
Chinese Office Action dated Jun. 20, 2016 in related Chinese Patent Application No. 201480007715.8.
English translation of International Preliminary Report on Patentability dated Aug. 20, 2015 together with the Written Opinion received in related International Application No. PCT/JP2014/051625.
International Search Report dated Apr. 15, 2014 issued in PCT/JP2014/051625.
Chinese Office Action dated Sep. 8, 2017 received in 20148007715.8.

* cited by examiner

BENDING APPARATUS WITH BENDING DIRECTION RESTRICTION MECHANISM

CROSS-REFERENCE TO RELATED APPLICATIONS

This application is a Continuation Application of PCT Application No. PCT/JP2014/051625, filed Jan. 27, 2014 and based upon and claiming the benefit of priority from the prior Japanese Patent Application No. 2013-021246, filed Feb. 6, 2013, the entire contents of both of which are incorporated herein by reference.

BACKGROUND OF THE INVENTION

1. Field of the Invention

The present invention relates to a bending apparatus which is mountable in, for example, an insertion section of an endoscope and includes a shape sensor for detecting a bending direction/curvature.

2. Description of the Related Art

Japanese Patent No. 4714570 discloses a shape detection probe which is assembled in a scope of an endoscope, bends as one-piece with the scope of the endoscope, and is used for detecting the shape of the scope. In this kind of shape detection probe, detection light, which is light for curvature detection and is emitted from a light source, is transmitted to a distal end through a light-supplying fiber. A mirror is provided at an emission end of the light-supplying fiber. Reflective light of the detection light, which is reflected by the mirror, is incident on a curvature detection fiber, and is received by a light reception element. A plurality of light loss portions, which absorb part of the reflective light, are provided near the surface of the curvature detection fiber. An absorption amount of the reflective light by the light loss portions varies depending on the curvature of a fiber bundle at locations where the light loss portions are provided. Thus, Japanese Patent No. 4714570 discloses a structure in which the curvature of the fiber bundle is calculated based on the intensity of the reflective light before and after the reflective light passes through the light loss portions.

BRIEF SUMMARY OF THE INVENTION

The sensitivity of the light loss portions, which are provided on the curvature detection fiber that constitutes the endoscope shape probe, has directivity to the bending direction of the endoscope in accordance with the direction of the light loss portions. In addition, it is desirable that the light loss portions be provided in parallel to an X axis and a Y axis which intersect at a center point O of the curvature detection fiber. However, in the structure of Japanese Patent No. 4714570, when the endoscope shape detection probe is disposed in the endoscope, even if such adjustment is made that the direction of possible bending of the endoscope (usually, at least one of an up-and-down direction and a left-and-right direction) and the X axis and Y axis of the curvature detection fiber become parallel, it is possible that the directions of sensitivity of all light loss portions do not become parallel to the direction of possible bending of the endoscope. Since the curvature detection fiber has directivity to the bending direction of the endoscope in accordance with the direction of the light loss portions, unless the directions of sensitivity of the light loss portions become parallel to the direction of possible bending of the endoscope, the dynamic range of the curvature detection fiber decreases and the detection sensitivity lowers. If the detection sensitivity lowers, for example, when the bending curvature is small (or bending R is large), there is a possibility that the bending shape cannot precisely be detected and it becomes difficult to exactly detect the shape of the endoscope.

The present invention has been made in consideration of the above circumstances, and the object of the invention is to provide a bending apparatus which can exactly detect the shape of bending equipment such as an endoscope.

A bending apparatus according to an aspect of the invention comprises: a shape sensor including a light source, an optical fiber configured to propagate desired detection light which is radiated from the light source, a detecting part disposed at a part of the optical fiber, and a light detector configured to detect the detection light propagated through the optical fiber, the shape sensor being configured to utilize a variation in optical characteristics, which is detected by the detecting part in accordance with a variation of curvature of the optical fiber when the optical fiber is bent, and the shape sensor being freely bendable in any direction and having directivity in detection sensitivity for a bending direction; and a bending direction restriction mechanism which is combined with the shape sensor and has bending directivity including such a property of ease in bending that bending is easy in at least a specific direction other than a direction of a center line, and such a property of difficulty in bending that bending is difficult in directions other than the specific direction.

In the above structure, a shape sensor, which is freely bendable in any direction and has directivity in detection sensitivity for a bending direction, is combined with a bending direction restriction mechanism having bending directivity. By restricting the direction of possible bending of the shape sensor to a high sensitivity direction by the bending direction restriction mechanism, the shape detection precision of the bending apparatus can be enhanced.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

[First Embodiment]
(Structure)

Figure 1:
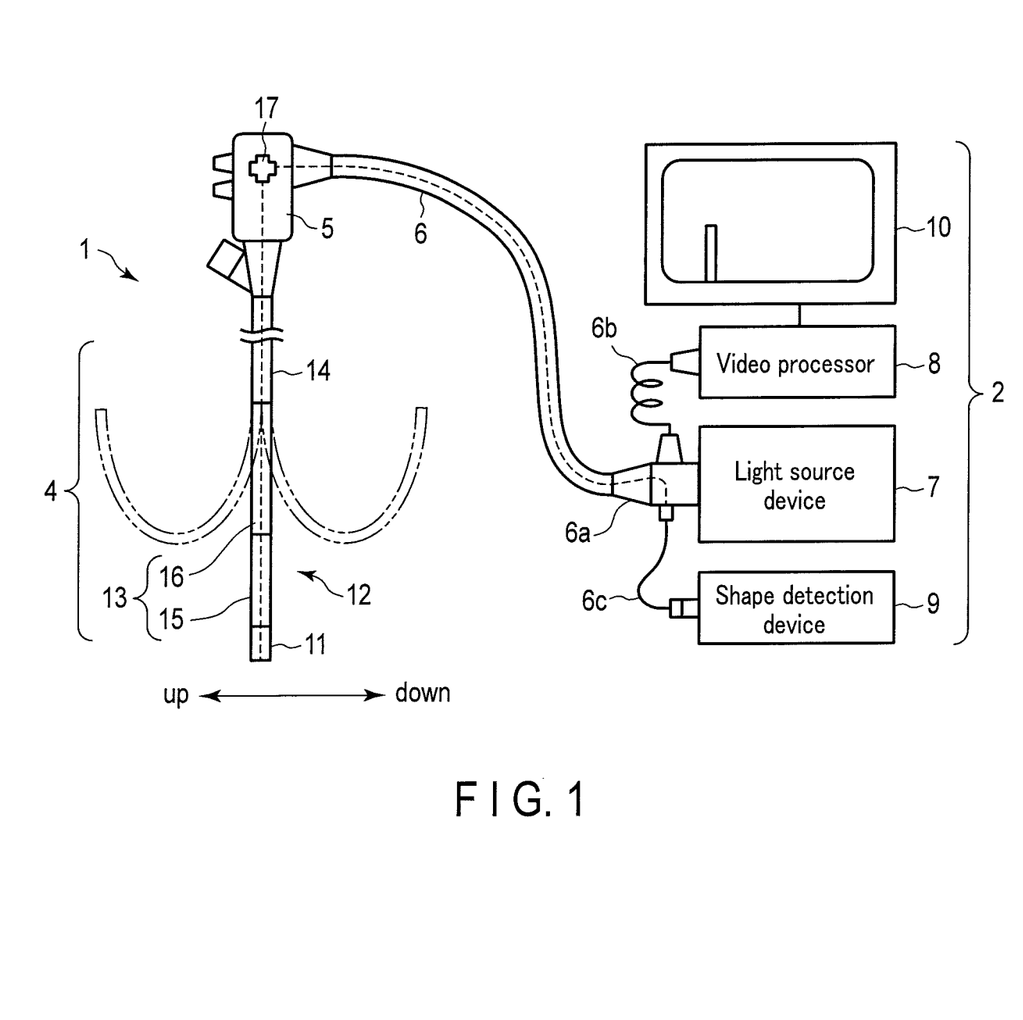
FIG. 1 is a schematic structural view of the entirety of a system of an endoscope according to a first embodiment of the present invention.

FIG. 1 to FIG. 5 illustrate a first embodiment of the present invention. This embodiment is an example of an application of a bending apparatus to an endoscope. FIG. 1 is a schematic structural view of the entirety of a system of an endoscope 1. The system of the endoscope 1 includes the endoscope 1 and a plurality of system constituent devices 2. The endoscope 1 includes a distal-end insertion tube 4, a hand operation unit 5, and a universal cord 6. The distal-end insertion tube 4 is elongated, and is mainly inserted in a tube cavity of the endoscope 1. The hand operation unit 5 is coupled to a proximal end portion of the distal-end insertion tube 4.

The system constituent devices 2 include a light source device 7, a video processor 8, a shape detection device 9, and a monitor 10. A connector portion 6a of the universal cord 6 is connected to the light source device 7, and is also connected to the video processor 8 and shape detection device 9 via electric cables 6b and 6c, respectively. By this structure, necessary signals are controlled in the light source device 7, video processor 8 and shape detection device 9.

Figure 2:
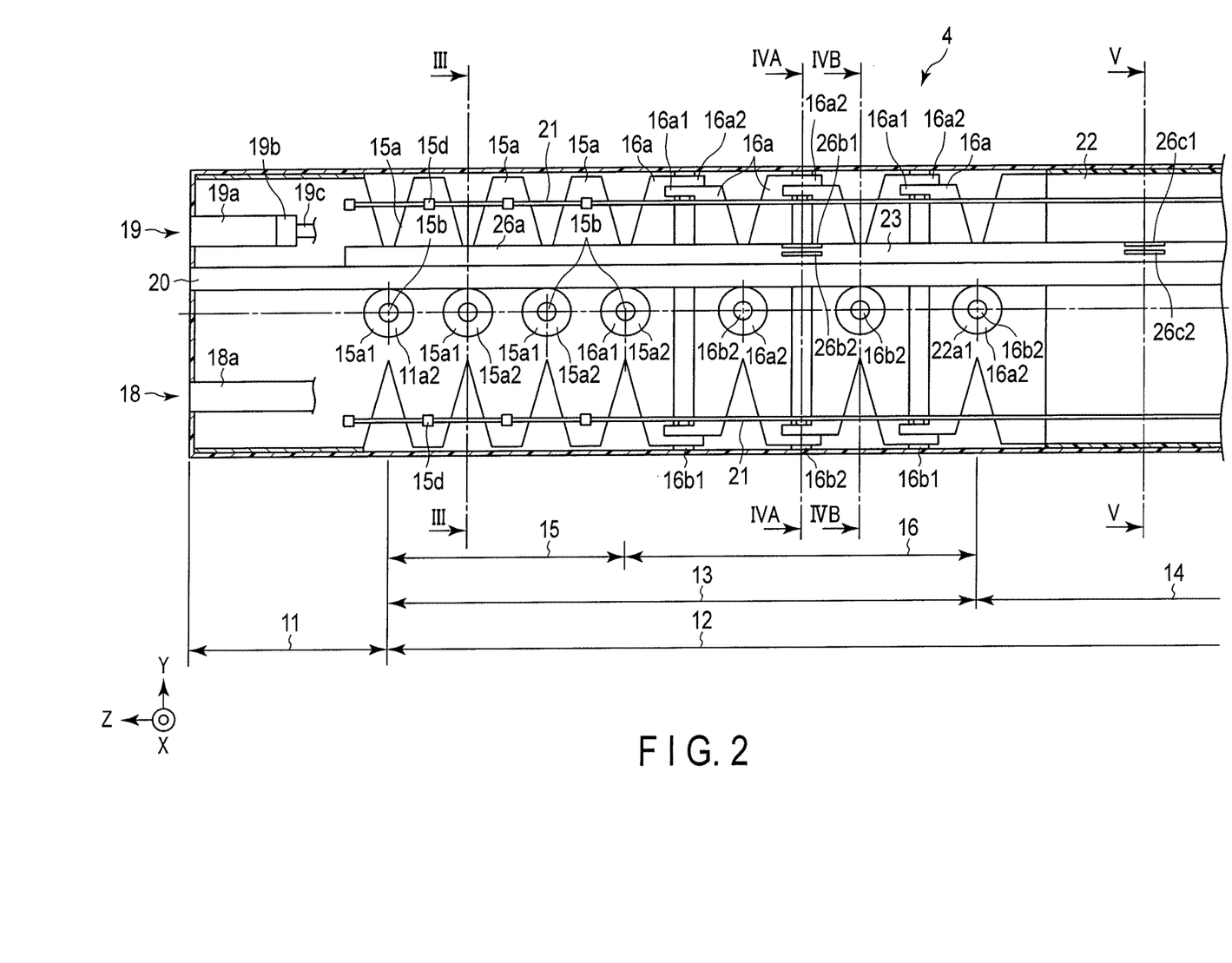
FIG. 2 is a vertical cross-sectional view illustrating an internal structure of a distal end portion of a distal-end insertion tube of the endoscope of the first embodiment.

The distal-end insertion tube 4 includes a rigid distal end section 11 and a flexible bending structure 12. As illustrated in FIG. 2, the distal end section 11 is provided with an illumination unit 18 and an observation unit 19. The illumination unit 18 is provided with a light guide 18a. A proximal end portion of the light guide 18a is provided to extend toward the connector portion 6a side of the universal cord 6. By the connection of the connector portion 6a to the light source device 7, illumination light, which is emitted from the light source device 7, is supplied to the illumination unit 18 through the light guide 18a, and is radiated to the outside from the illumination unit 18. The observation unit 19 is provided with an objective optical system 19a and an image sensor 19b. An endoscopic observation image, which is formed on the image sensor 19b and is image information of the front side of the distal end section 11, is converted to an image signal by photoelectric conversion. The image signal from the image sensor 19b is transmitted to the video processor 8 side via a signal line 19c. Thereby, an endoscopic observation image is displayed on the monitor 10.

The flexible bending structure 12 functions as a main body of a bending direction restriction mechanism which has bending directivity including a property of ease in bending and a property of difficulty in bending. The property of ease in bending is such a property that bending is easy in at least a specific direction other than a direction of a center line (Z-axis direction in FIG. 2 to FIG. 5). The property of difficulty in bending is such a property that bending is difficult in directions other than the specific direction. The flexible bending structure 12 includes a bending restriction section 13 and a free bending section 14. The bending restriction section 13 includes an operational bending section 15 and a second bending section 16. The operational bending section 15 includes a two-directional bending section which is bendable in two directions, for example, up and down (up-down) directions of the endoscope 1. The second bending section 16 includes a four-directional bending section which is bendable in four directions, for example, the up and down (up-down) directions and left and right (left-right) directions of the endoscope 1.

The hand operation unit 5 is provided with a bending operation dial 17. The bending restriction section 13 is configured to bend in desired two directions (up-down) with a desired curvature, by the operation of the dial 17 of the hand operation unit 5.

Referring to FIG. 2, the internal structure of the distal-end insertion tube 4 is described. In the distal end section 11, there are provided the illumination unit 18, the observation unit 19, a channel 20 for insertion of a therapeutic device, in which a therapeutic device (not shown) or the like can be inserted, a nozzle (not shown) for feeding air/water, and an opening portion (not shown) for feeding jet water. A distal end portion of the operational bending section 15 is coupled to the rear end side of the distal end section 11.

Figure 3:
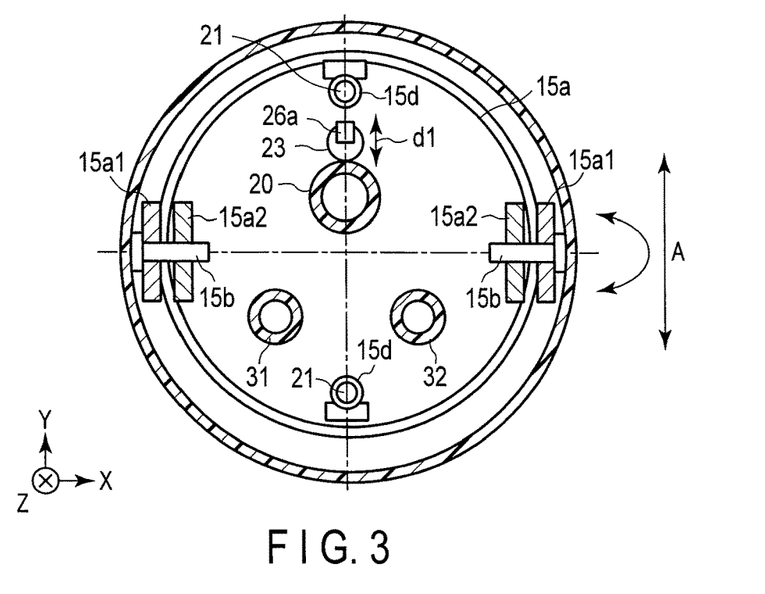
FIG. 3 is a cross-sectional view taken along line III-III in FIG. 2.

The operational bending section 15 is a coupling structure of annular members 15a, in which a plurality of annular members 15a are juxtaposed along the center line direction (Z-axis direction in FIG. 2 to FIG. 5) of the flexible bending structure 12. A pair of front projection portions 15a1 each projecting forward and having a tongue-like shape are formed at a front end portion of each annular member 15a, and a pair of rear projection portions 15a2 each projecting rearward and having a tongue-like shape are formed at a rear end portion of each annular member 15a. The paired front projection portions 15a1 are disposed at positions of 180°, with the center axis of each annular member 15a being interposed. Similarly, the paired rear projection portions 15a2 are disposed at positions of 180°, with the center axis of each annular member 15a being interposed. In addition, the paired front projection portions 15a1 and the paired rear projection portions 15a2 of each annular member 15a are disposed at corresponding positions in the front-and-rear direction (the same position in the circumferential direction of each annular member 15a). As illustrated in FIG. 3, rotational shafts 15b for bending in the up-and-down direction, such as hinge pins or rivets, are inserted in portions (two locations) at which the rear projection portions 15a2 of a front-side annular member 15a of neighboring annular members 15a and the front projection portions 15a1 of a rear-side annular member 15a of the neighboring annular members 15a are laid over each other. Thereby, the front-side and rear-side annular members 15a are coupled to be rotatable only in one direction about the rotational shafts 15b (about the X axis in FIG. 2 and FIG. 3). Hence, as indicated by an arrow A in FIG. 3, the direction of easy bending is restricted by the operational bending section 15 to only one direction relative to the direction about the axis of the center line of the flexible bending structure 12, and a one-directional bending restriction section, which can bend in two directions, i.e. up and down (up-down) directions of the endoscope 1, is formed.

Rear projection portions 11a2 of the same structure as the rear projection portions 15a2 of the annular member 15a are projectingly provided on the rear end side of the distal end section 11. Rotational shafts 15b for the up-and-down direction are inserted in portions (two locations) at which the rear projection portions 11a2 and the front projection portions 15a1 of the annular member 15a at the frontmost position of the operational bending section 15 are laid over each other. Thereby, the rear side of the distal end section 11 and the annular member 15a at the frontmost position of the operational bending section 15 are coupled to be rotatable only in one direction about the rotational shafts 15b (about the X axis in FIG. 2 and FIG. 3).

Furthermore, two wire holding members 15d are fixed to an inner peripheral surface of the annular member 15a. These two wire holding members 15d are disposed at positions of 180° with respect to the center axis of each annular member 15a and at a middle position between the paired front projection portions 15a1 (i.e. at a position of 90° relative to the front projection portion 15a1 in the circumferential direction).

Distal end portions of the two operation wires 21, which are inserted through the respective wire holding members 15d, are fixed to the distal end section 11. Proximal end portions of the two operation wires 21 are coupled to an up-and-down bending operation knob of the dial 17 of the hand operation unit 5. The operational bending section 15 is configured to bend at a desired angle in the up-and-down rotational direction about the rotational shafts 15b as the X axis, if the dial 17 is operated. A distal end portion of the second bending section 16 is coupled to the rear end side of the operational bending section 15.

The second bending section 16 is a coupling structure of annular members 16a, in which a plurality of annular members 16a are juxtaposed along the center line direction of the flexible bending structure 12. A pair of front projection portions 16a1 each projecting forward and having a tongue-like shape are formed at a front end portion of each annular member 16a, and a pair of rear projection portions 16a2 each projecting rearward and having a tongue-like shape are formed at a rear end portion of each annular member 16a. The paired front projection portions 16a1 are disposed at positions of 180° in the circumferential direction of each annular member 16a. Similarly, the paired rear projection portions 16a2 are disposed at positions of 180° in the circumferential direction of each annular member 16a.

Figure 4A:
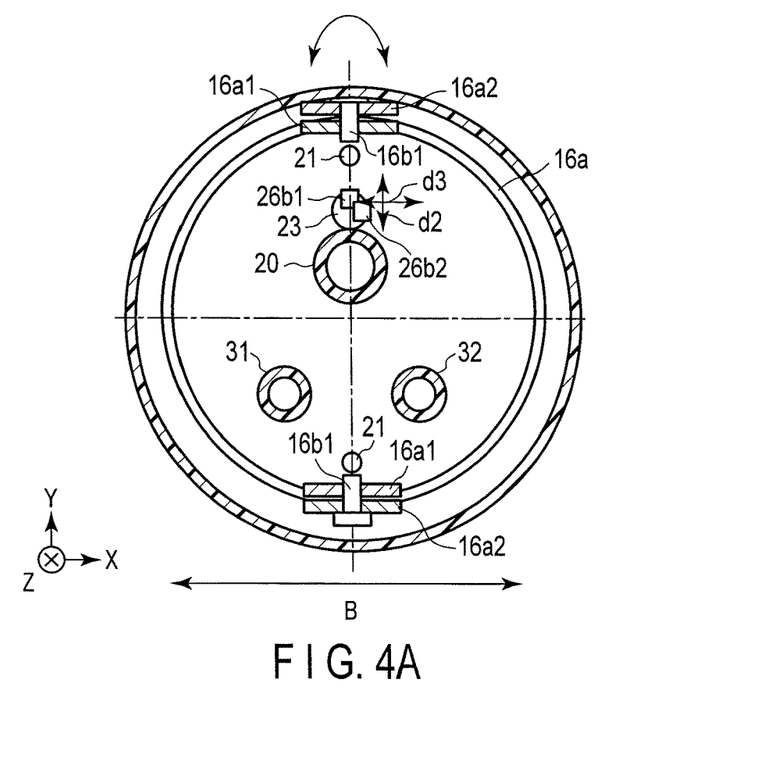
FIG. 4A is a cross-sectional view taken along line IVA-IVA in FIG. 2.

In addition, in the second bending section 16, the paired front projection portions 16a1 and the paired rear projection portions 16a2 of each annular member 16a are disposed at positions displaced by 90° from the corresponding positions in the front-and-rear direction (the same position in the circumferential direction of each annular member 16a). As illustrated in FIG. 4A, rotational shafts 16b1 for bending in the left-and-right direction, such as hinge pins or rivets, are inserted in portions (two locations) at which the rear projection portions 16a2 of a front-side annular member 16a of neighboring annular members 16a and the front projection portions 16a1 of a rear-side annular member 16a of the neighboring annular members 16a are laid over each other. Thereby, the front-side and rear-side annular members 16a are coupled to be rotatable only in one direction about the rotational shafts 16b1 (about the Y axis in FIG. 2 and FIG. 4A).

Figure 4B:
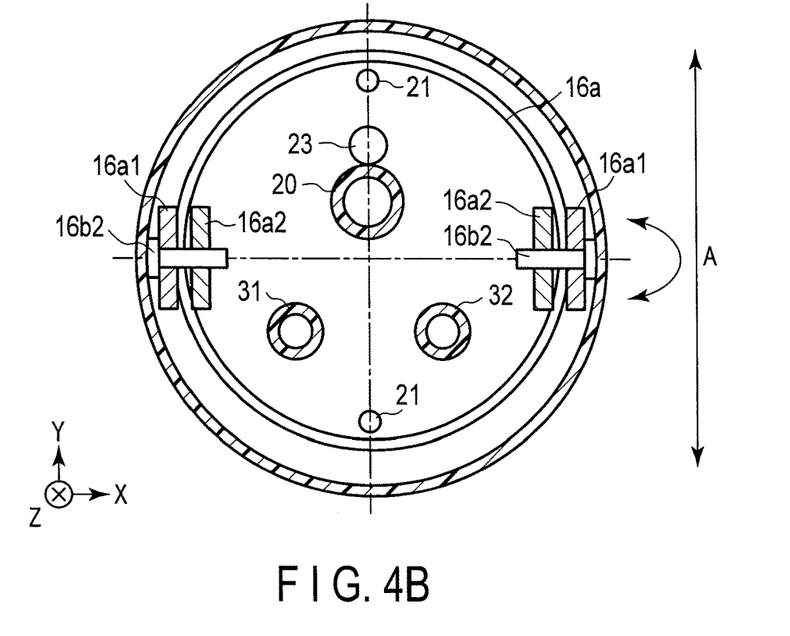
FIG. 4B is a cross-sectional view taken along line IVB-IVB in FIG. 2.

In the second bending section 16, the paired front projection portions 16a1 and the paired rear projection portions 16a2 of each annular member 16a are disposed at positions displaced by 90° from the corresponding positions in the front-and-rear direction (the same position in the circumferential direction of each annular member 16a). Thereby, as illustrated in FIG. 4B, rotational shafts 16b2 for bending in the up-and-down direction are disposed adjacent to the rotational shafts 16b1 for bending in the left-and-right direction. The paired front projection portions 16a1 and the paired rear projection portions 16a2 are coupled to be rotatable only in one direction about the rotational shafts 16b2 for the up-and-down direction (about the X axis in FIG. 2 and FIG. 4A). Thus, in the second bending section 16, the rotational shafts 16b1 for the left-and-right direction and the rotational shafts 16b2 for the up-and-down direction are alternately arranged along the center line direction of the flexible bending structure 12. Thereby, the directions of easy bending are restricted to the four directions, i.e. the up-and-down directions and left-and-right directions of the endoscope 1, by the second bending section 16, and a two-directional bending restriction section is formed in which the directions of easy bending are restricted to the two directions of up and down directions (up-down) of the endoscope 1, which are indicated by an arrow A in FIG. 4B, and the two directions of left and right directions (left-right), which are indicated an arrow B in FIG. 4A, relative to the direction about the axis of the center line of the flexible bending structure 12.

At a coupling part between the rear end side of the operational bending section 15 and the distal end portion of the second bending section 16, rotational shafts 16b2 for bending in the up-and-down direction are inserted in portions (two locations) at which the rear projection portions 15a2 of the annular member 15a at the rearmost position of the operational bending section 15 and the front projection portions 16a1 of the annular member 16a at the frontmost position of the second bending section 16 are laid over each other. By this structure, the annular member 15a at the rearmost position of the operational bending section 15 and the annular member 16a at the frontmost position of the second bending section 16 are coupled to be rotatable only in one direction about the rotational shafts 16b2 (about the X axis in FIG. 2 and FIG. 4B).

Since the operation wires 21 are not connected to the annular members 16a of the second bending section 16, the annular members 16a do not rotate even if the operation wires 21 are pulled and operated. On the other hand, if an external force acts on the distal-end insertion tube 4, for example, by the distal-end insertion tube 4 being pressed on an external structure, the annular members 16a of the second bending section 16 rotate in two desired directions (directions of rotation about the X axis and Y axis in FIG. 4A and FIG. 4B) about the rotational shafts 16b1 for the left-and-right direction and rotational shafts 16b2 for the up-and-down direction. A distal end portion of the free bending section 14 is coupled to the rear end side of the second bending section 16.

Figure 5:
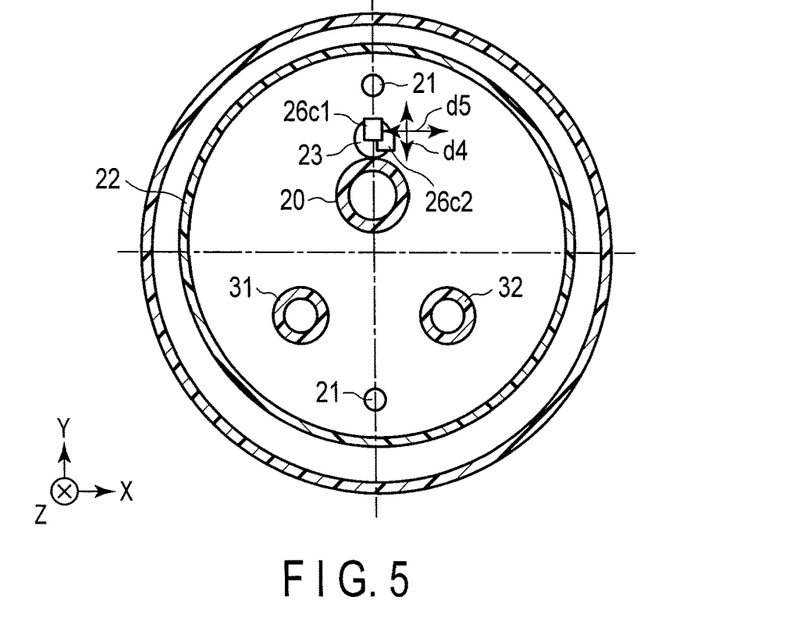
FIG. 5 is a cross-sectional view taken along line V-V in FIG. 2.

The free bending section 14 includes, as illustrated in FIG. 5, a flexible tube 22, such as a fluororesin tube, which is freely bendable in any direction and around which, for example, a buckling prevention coil is wound. Since the operation wires 21 are not connected to the free bending section 14, either, the free bending section 14 cannot be bent by the operation of the dial 17 shown in FIG. 1. On the other hand, the free bending section 14, too, bends in a free shape, for example, in accordance with the shape of an external structure in which the distal-end insertion tube 4 is inserted.

Front projection portions 22a1, which have the same structure as the front projection portions 16a1 of the annular member 16a, are projectingly provided at a distal end portion of the free bending section 14. Rotational shafts 16*b*2 for the up-and-down direction are inserted in portions (two locations) at which the front projection portions 22*a*1 and the rear projection portions 16*a*2 of the annular member 16*a* at the rearmost position of the second bending section 16 are laid over each other, and the rear end side of the distal end section 11 and the annular member 15*a* at the frontmost position of the operational bending section 15 are coupled to be rotatable only in one direction about the rotational shafts 16*b*2 (about the X axis in FIG. 2 and FIG. 3).

Figure 6:
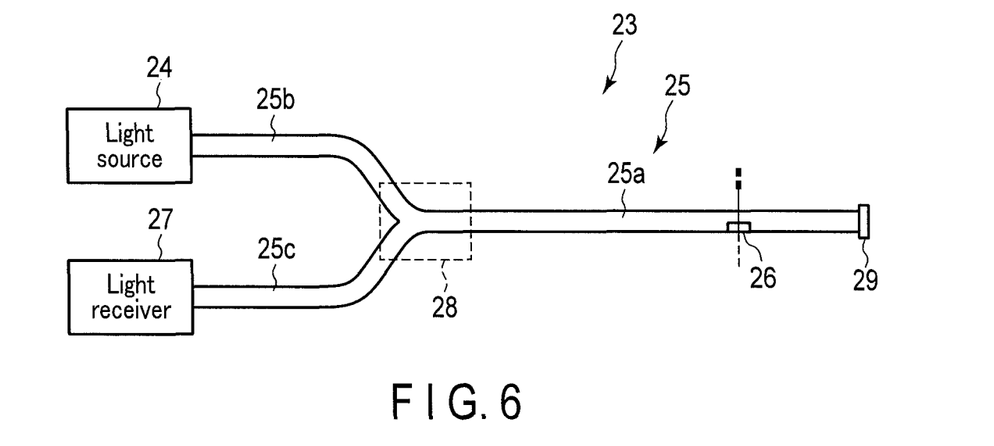
FIG. 6 is a schematic structural view illustrating a shape sensor of a bending apparatus of the first embodiment.

In addition, the bending apparatus of the present embodiment is configured such that the flexible bending structure 12 and a shape sensor 23 illustrated in FIG. 6 are combined. The shape sensor 23 mainly includes a light source 24 which emits light, an optical fiber 25 which guides light that is emitted from the light source 24, a detecting part 26, and a light receiver (light detector) 27 which detects detection light propagated through the optical fiber 25. The light source 24 is, for instance, a light-emitting diode (LED) or a laser light source.

Figure 7:
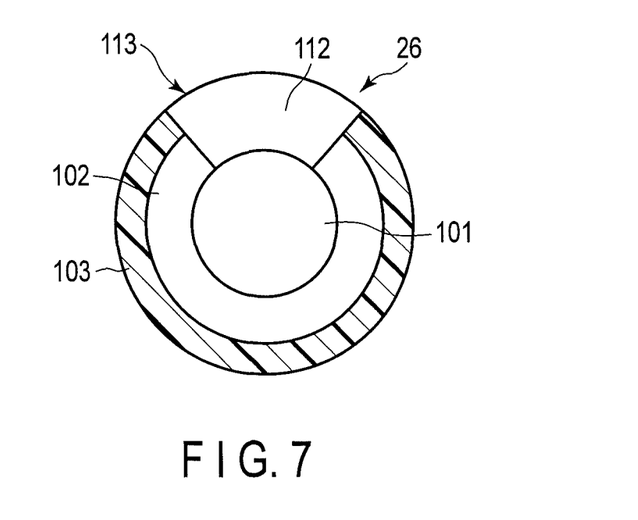
FIG. 7 is a transverse cross-sectional view of a detection part of the shape sensor of the bending apparatus of the first embodiment.

The optical fiber 25 is branched, at a coupling portion 28, into three optical fibers, namely a detection optical fiber 25*a*, a light supply optical fiber 25*b*, and a light reception optical fiber 25*c*. A reflector 29 for reflecting guided light is provided at a distal end of the detection optical fiber 25*a*. As illustrated in FIG. 7, the optical fiber 25 includes a core 101, and a clad 102 which covers the outer periphery of the core 101. The optical fiber 25 may include a sheath member 103 as an outermost sheath.

The coupling portion 28 is formed such that two light guide members, namely the light supply optical fiber 25*b* and light reception optical fiber 25*c*, are connected to one light guide member, namely the detection optical fiber 25*a*. The light supply optical fiber 25*b* is a light input path, and guides light, which is emitted from the light source 24 provided at an end portion thereof, to the coupling portion 28. The coupling portion 35 guides most of the light, which is incident from the light supply optical fiber 25*b*, to the detection optical fiber 25*a*, and guides at least part of the light, which is reflected by the reflector 29, to the light reception optical fiber 25*c*.

In the shape sensor 23 of the present embodiment, the detection optical fiber 25*a* is integrally mounted along an object, for example, the elongated, flexible bending structure 12. Thereby, the bending state and bending direction of the flexible bending structure 12 are detected. When the shape sensor 23 is mounted on the object, a bending portion of the object is aligned with the detecting part 26 of the shape sensor 23. Thereby, the shape sensor 23 is disposed at a proper position of the object. The detection optical fiber 25*a* follows a flexible movement of the object, reflects the light, which is incident from the light supply optical fiber 25*b*, by the reflector 29, and reciprocally guides the light. Specifically, the detection optical fiber 25*a* guides the light, which comes from the light supply optical fiber 25*b* via the coupling portion 28, to the reflector 29, and guides the reflective light, which is reflected by the reflector 29, back to the coupling portion 28.

The light reception optical fiber 25*c* is a light output path, and guides the reflective light, which is reflected by the reflector 29 and is branched at the coupling portion 28, to the light receiver 27 that is provided at the end portion thereof. The detection optical fiber 25*a* includes at least one detecting part 26.

As illustrated in FIG. 7, the detecting part 26 includes an aperture portion 112 and an optical characteristic conversion member 113. The aperture portion 112 is formed by removing a part of the clad 102 from the outer periphery of the detection optical fiber 25*a*. In FIG. 7, a part of the core 101 is exposed. However, even if the core 101 is not exposed, it should suffice if such formation is adopted such that light, which passes through the light guide, reaches the aperture portion 112.

The optical characteristic conversion member 113 includes a function of converting the characteristics of the guided light. The optical characteristic conversion member 113 is, for example, a guided light losing member or a wavelength conversion member. In the case of the guided light losing member, a light absorber may be taken as an example. In the case of the wavelength conversion member, a phosphor may be taken as an example. In the present embodiment, the optical characteristic conversion member is treated as the guided light losing member.

Light, which is radiated from the light source 24, is guided through the light supply optical fiber 25*b*, coupling portion 28 and detection optical fiber 25*a*, and is reflected by the reflector 29. The reflective light, which is reflected by the reflector 29, is branched at the coupling portion 28 as detection light, which reaches the light receiver 27 via the light reception optical fiber 25*c*. The light receiver 27 photoelectrically converts the received detection light, and outputs an electric signal indicative of a light amount.

In the shape sensor 23 of the present embodiment, a loss occurs when the light passing through the optical fiber 25 has been incident on the optical characteristic conversion member 113. The guided light loss amount varies depending on the direction of bending and shaking and the amount of bending of the light reception optical fiber 25*c*.

Even if the detection optical fiber 25*a* has a straight line shape, a certain amount of light is lost by the optical characteristic conversion member 113 in accordance with the width of the aperture portion 112. When this light loss amount is set as a reference, for example, if the optical characteristic conversion member 113 is disposed on the outer peripheral surface in the bending direction of the detection optical fiber 25*a* which bends, a guided light loss amount, which is greater than the guided light loss amount that is set as the reference, occurs. Conversely, if the optical characteristic conversion member 113 is disposed on the inner peripheral surface in the bending direction of the detection optical fiber 25*a* which bends, a guided light loss amount, which is less than the guided light loss amount that is set as the reference, occurs.

A variation in this guided light loss amount is reflected on a detection light amount which is received by the light receiver 27. Specifically, the variation in the guided light loss amount is reflected on an output signal of the light receiver 27. Accordingly, it is possible to detect, based on the output signal of the light receiver 27, the bending direction and bending amount (angle) at the position of the detecting part 26 of the shape sensor 23, that is, at the position of the object, where the optical characteristic conversion member 113 is provided.

In the shape sensor 23, for example, the detection optical fiber 25*a* is integrally mounted along the object which is the elongated, flexible member. Thereby, the bending state and bending direction of the object are detected. In addition, when the shape sensor 23 is mounted on the object, the bending portion of the object is aligned with the detecting part 26 of the shape sensor 23, and thereby the detecting part 26 is disposed at a proper position of the object. In the bending apparatus of the present embodiment, at least a part of the detection optical fiber 25*a* of the shape sensor 23 is fixed and held, by an adhesive or the like, to the channel 20 which is disposed within the flexible bending structure 12.

Furthermore, in the shape sensor 23 that is used in the bending apparatus of the present embodiment, at least one detecting part 26a is disposed in the range of the operational bending section 15, at least two detecting parts 26b1 and 26b2 are disposed in the range of the second bending section 16, and at least two detecting parts 26c1 and 26c2 are disposed in the range of the free bending section 14.

Figure 8:
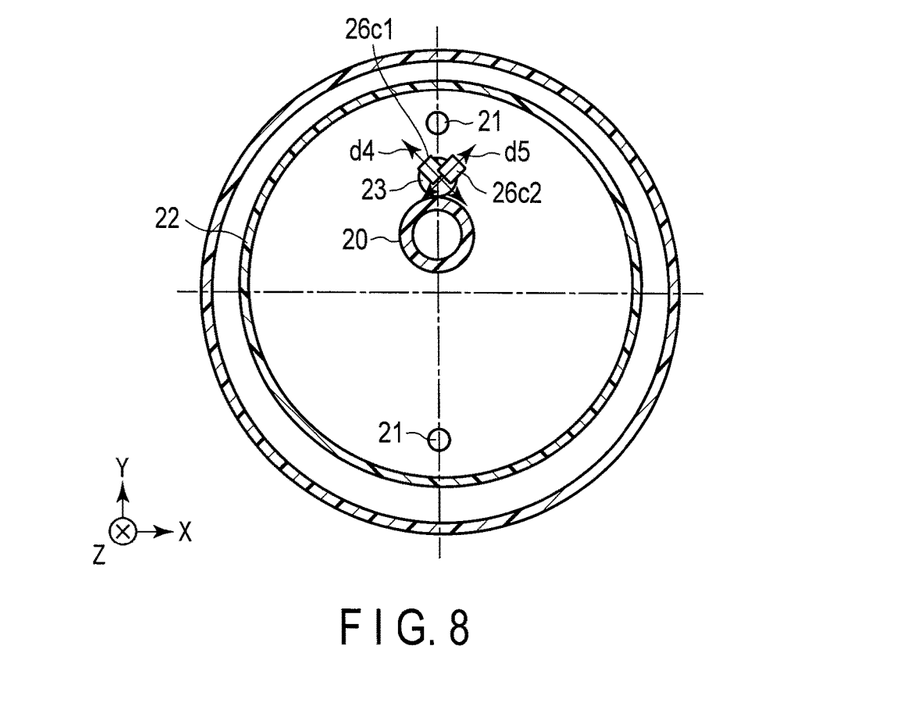
FIG. 8 is a transverse cross-sectional view of a main part illustrating a modification of an internal structure of a free bending section of the distal-end insertion tube of the endoscope of the first embodiment.

The detecting part 26a, detecting parts 26b1 and 26b2 and detecting parts 26c1 and 26c2 similarly have directivity in sensitivity of detection of curvature. The detecting part 26a is disposed such that the direction in which the detection sensitivity becomes maximum is parallel to the bending direction specified by the rotational shafts 15b for bending in the up-and-down direction. In addition, the detecting part 26b1 and 26b2 is disposed such that the direction in which the detection sensitivity becomes maximum is parallel to the bending directions specified by the rotational shafts 16b1 for bending in the left-and-right direction and the rotational shafts 16b2 for bending in the up-and-down direction. Since the rotational shafts 16b1 and 16b2 are alternately arranged in a manner to cross at about 90°, the detecting part 26b1 (first detecting part), which is one of the detecting parts 26b1 and 26b2, is disposed in parallel to the X axis, and the other detecting part 26b2 (second detecting part) is disposed in parallel to the Y axis. Similarly, the detecting part 26c1, which is one of the detecting parts 26c1 and 26c2, is disposed in parallel to the X axis, and the other detecting part 26c2 is disposed in parallel to the Y axis. However, it is not always necessary that the detecting parts 26c1 and 26c2, which are disposed in the free bending section 14, be disposed in parallel to the X axis and Y axis. For example, as in a modification illustrated in FIG. 8, the detecting parts 26c1 and 26c2 may be disposed at angles different from the X axis and Y axis. It is desirable, however, that the angle formed between the paired detecting parts 26c1 and 26c2 be about 90°, with the Z axis being set to be the center.

Although each of the detecting part 26a of the operational bending part, the detecting part 26b1 and 26b2 of the second bending section 16 and the detecting part 26c1 and 26c2 of the free bending section 14 is disposed at one location in the Z-axis direction in FIG. 2 in the present embodiment, these may be disposed at a plurality of locations where necessary (for example, in accordance with the length, etc.).

In addition, in the present embodiment, although the shape sensor 23 is disposed on the channel 20, the shape sensor 23 may be disposed on some other bendable built-in member provided within the flexible bending structure 12, for example, as illustrated in FIG. 3 to FIG. 5, on an A/W tube 31 for feeding air/water, which is connected to an air/water feeding nozzle of the distal end section 11, or a J tube 32 for feeding jet water, which is connected to a jet water feeding opening portion of the distal end section 11.

(Operations)

Next, the operations of the above-described structures will be described.

(Operation in Operational Bending Section 15)

Referring to FIG. 2 and FIG. 3, the operation in the operational bending section 15 of the present embodiment is described. The plural annular members 15a, which constitute the operational bending section 15, are coupled to be rotatable about the rotational shafts 15b which are coaxially disposed. Thus, as indicated by arrow A in FIG. 3, the one-directional bending restriction section for the Y-axis direction is formed in the direction of easy bending of the operational bending section 15 which is composed of the annular members 15a. Thus, if the operational bending section 15 bends, the shape sensor 23, which is disposed on the built-in channel 20, also bends in a similar shape to the operational bending section 15. At this time, a detection-directivity direction d1 of the detecting part 26a, which is provided in the shape sensor 23, is parallel to (agrees with) the direction of easy bending of the operational bending section 15, which is indicated by arrow A in FIG. 3. Thus, the curvature of the operational bending section 15 can be detected with the highest sensitivity.

(Operation in Second Bending Section 16)

Referring to FIG. 2 and FIGS. 4A and 4B, the operation in the second bending section 16 is described. In the second bending section 16, the rotational shafts 16b1 for the left-and-right direction and the rotational shafts 16b2 for the up-and-down direction are alternately arranged along the center-axis direction of the flexible bending structure 12. Thereby, the easy bending directions are restricted to the four directions, i.e. the up and down directions and the left and right directions, of the endoscope 1 by the second bending section 16. Specifically, the easy bending directions are restricted to the two directions (directions parallel to the Y axis) of the up and down (up-down) directions of the endoscope 1, which are indicated by arrow A in FIG. 4B, relative to the direction about the axis of the center line of the flexible bending structure 12, and to the two directions (directions parallel to the X axis) of the left and right (left-right) directions indicated by arrow B in FIG. 4A. Thus, if the second bending section 16 bends, the shape sensor 23, which is disposed on the built-in channel 20, also bends in a similar shape to the second bending section 16. At this time, a detection-directivity direction d2 of the detecting part 26b1, which is one of the detecting parts provided in the shape sensor 23, is parallel to (agrees with) the direction of easy bending, which is indicated by arrow A in FIG. 4B and is parallel to the X axis about the rotational shafts 16b2 for the up-and-down direction. Similarly, a detection-directivity direction d3 of the detecting part 26b2, which is the other of the detecting parts provided in the shape sensor 23, is parallel to (agrees with) the direction of easy bending, which is parallel to the Y axis about the rotational shafts 16b1 for the left-and-right direction indicated by arrow B in FIG. 4A. Thus, the curvature of the second bending section 16 can be detected with the highest sensitivity.

(Operation in Free Bending Section 14).

The operation in the free bending section 14 is described with reference to FIG. 2 and FIG. 5. The flexible tube 22 is freely bendable in any direction, and is not provided with a bending restriction portion such as the one-directional bending restriction section of the operational bending section 15 or the two-directional bending restriction section of the second bending section 16. Thus, there is no direction of easy bending, and free bending in any direction is possible. Detection-directivity directions d4 and d5 of the detecting parts 26c1 and 26c2, which are provided in the range of the free bending section 14 of the shape sensor 23, are set to be parallel to the X axis and Y axis (intersection at 90°) like the detecting part 26a and detecting part 26b1, 26b2. Thus, the bending direction and curvature of the free bending section 14 can be detected even if the free bending section 14 is bent in any direction, if calculated based on the outputs of the detecting part 26c1, 26c2.

In the manner as described above, the bending direction and curvature of the flexible bending structure 12 can be detected by the shape sensor 23, and the shape of the distal-end insertion tube 4 of the endoscope 1 can be detected. In particular, as regards the bending restriction section 13 for which the direction of easy bending is determined, this shape can be detected by utilizing the detection sensitivity of the shape sensor 23 at maximum.

(Advantageous Effects)

With the above-described structure, the following advantageous effects can be obtained. Specifically, in the bending apparatus of the present embodiment, the easy bending direction of the endoscope 1 and the detection-directivity direction of the shape sensor 23 are parallel in the bending direction restriction range of the flexible bending structure 12. Thus, the shape of the endoscope 1 can be detected in the state in which the detection sensitivity of the shape sensor 23 is enhanced as high as possible (in a wide dynamic range). It is possible, therefore, to provide the endoscope 1 in which it is highly possible that the shape of the distal-end insertion tube 4 of the endoscope 1 can be detected more precisely, even with a small bending curvature of the endoscope 1 (or large bending R).

[Second Embodiment]

(Structure)

Figure 9:
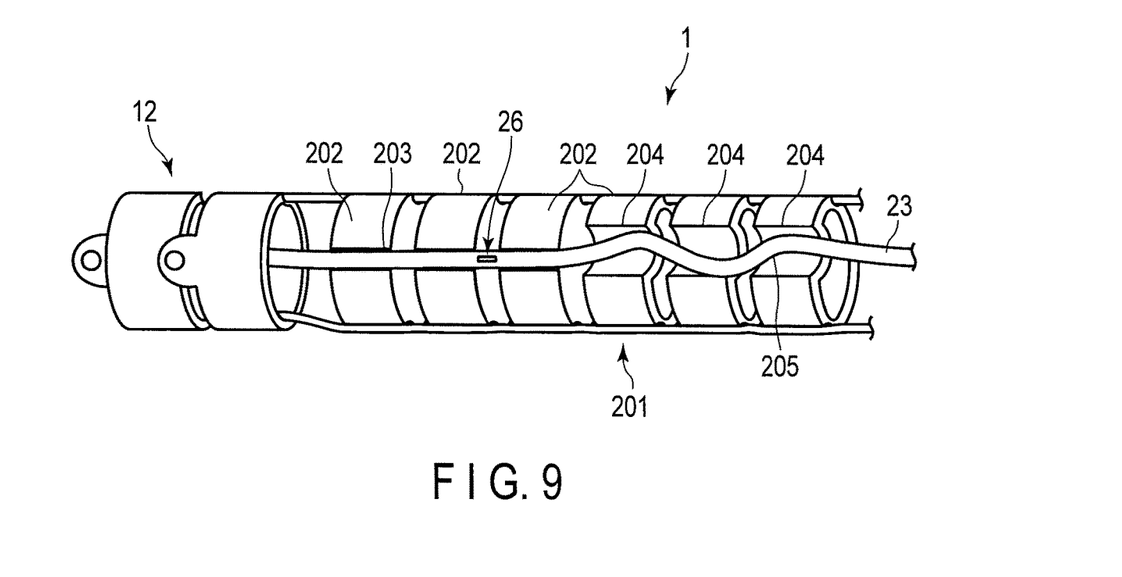
FIG. 9 is a perspective view of a main part illustrating a bending section of an endoscope of a second embodiment of the invention.
Figure 10A:
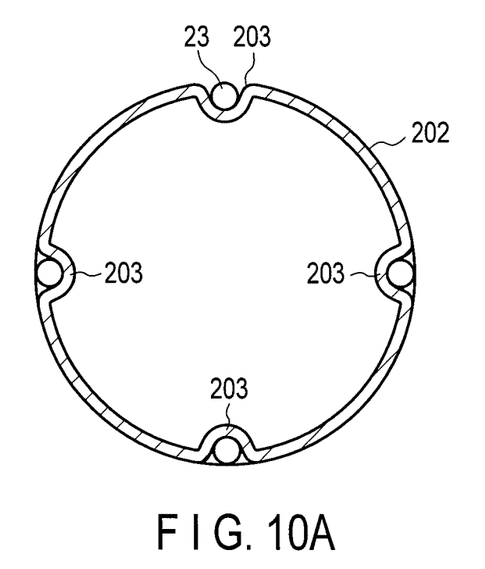
FIG. 10A is a transverse cross-sectional view illustrating a sensor holding recess portion of an annular member of the endoscope of the second embodiment.

FIG. 9 and FIG. 10A illustrate a second embodiment of the present invention. This embodiment is a modification of the structure of the endoscope 1 of the first embodiment (see FIG. 1 to FIG. 7), which is altered as described below.

Specifically, as illustrated in FIG. 9, in the endoscope 1 of this embodiment, a plurality of sensor holding recess portions 203, namely, four sensor holding recess portions in this embodiment, are formed in a bending section 201 constituting the bending restriction section 13 of the flexible bending structure 12. The sensor holding recess portions 203 are formed by recessing inward the outer peripheral surfaces of a plurality of annular members 202 which are juxtaposed along the center line direction of the flexible bending structure 12, as illustrated in FIG. 10A. The four sensor holding recess portions 203 are disposed at intervals of, for example, 90° in the peripheral direction of the annular members 202.

The shape sensor 23 is directly or indirectly accommodated in each of the sensor holding recess portions 203, and the shape sensor 23 and annular member 202 are fixed at least at one location by, for example, an adhesive. In addition, large-width portions 204, which are formed by making the groove width of the sensor holding recess portions 203 greater than the shape sensor 23, are formed in some of the plural annular members 202. In addition, a slack 205 is formed on the shape sensor 23 that is accommodated in the large-width portions 204.

(Operation and Advantageous Effect)

In the present embodiment, since the shape sensor 23 is held by the annular members 202 of the bending section 201, the shape sensor 23 directly bends following (according to) the bending operation of the flexible bending structure 12 in accordance with the rotational operation of the annular members 202. Thus, unlike the case in which the shape sensor 23 is fixed to the channel 20 provided within the flexible bending structure 12, there is a less possibility of non-uniform bending within the flexible bending structure 12, and the bending shape of the flexible bending structure 12 can more exactly be detected. Therefore, in the present embodiment, in addition to the advantageous effects of the first embodiment, the shape of the distal-end insertion tube 4 can more exactly be detected.

Figure 10B:
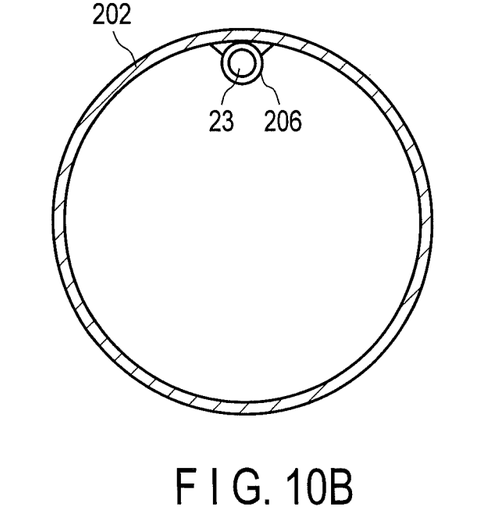
FIG. 10B is a transverse cross-sectional view illustrating a cylindrical holding member of the annular member.

In the meantime, the present invention is not limited to the above-described embodiments. For example, as in a modification of the second embodiment, which is illustrated in FIG. 10B, such a configuration may be adopted that a sensor-holding cylindrical holding member 206 is provided on the inner peripheral surface of each annular member 202 of the bending section 201, and the shape sensor 23 is passed through this sensor-holding cylindrical holding member 206. Thereby, the shape sensor 23 is held in the annular members 202 of the bending part 201. In addition, the structure, in which the sensor-holding cylindrical holding member 206 is provided on the inner peripheral surface of each annular member 202 of the bending section 201, and the structure, in which the sensor holding recess portions 203 are provided on the outer peripheral surface side of the annular members 202, may be provided in combination. In addition, such a configuration may be adopted that the shape sensor 23 is directly or indirectly accommodated in either the sensor holding recess portions 203 or the sensor-holding cylindrical holding member 206, or in these combined, and the shape sensor 23 and annular members 202 are held and fixed by, for example, an adhesive, at least at one location. Besides, needless to say, various modifications may be implemented without departing from the spirit of the present invention.

What is claimed is:

1. A bending apparatus comprising:
   a shape sensor including a light source, an optical fiber configured to propagate desired detection light which is radiated from the light source, a detecting part disposed at a part of the optical fiber, and a light detector configured to detect the detection light propagated through the optical fiber, the shape sensor being configured to utilize a variation in optical characteristics, which is detected by the detecting part in accordance with a variation of curvature of the optical fiber when the optical fiber is bent, and the shape sensor being freely bendable in any direction and having directivity in detection sensitivity for a bending direction; and
   a bending direction restriction mechanism which is combined with the shape sensor and has bending directivity including such a property of ease in bending that bending is easy in at least a specific direction other than a direction of a center line, and such a property of difficulty in bending that bending is difficult in directions other than the specific direction,
   wherein the shape sensor is configured such that the optical fiber is integrally mounted to be in line with the bending direction restriction mechanism, and the detecting part and a bending portion of the bending direction restriction mechanism are aligned, wherein the shape sensor has different directivity of detection sensitivity of the detecting part, relative to a bending direction of the optical fiber, and a detection-directivity direction, in which the detection sensitivity is highest, substantially agrees with a direction of easy bending of the bending direction restriction mechanism in at least a certain range in the direction of the center line of the bending direction restriction mechanism,
   wherein at least a part of the bending direction restriction mechanism includes a one-directional bending restriction section in which the direction of easy bending is restricted to only one direction relative to a direction about an axis of the center line of the bending direction restriction mechanism, or a two-directional bending restriction section in which the direction of easy bending is restricted to two directions, and a free bending section which is freely bendable in all directions relative to the direction about the axis of the center line of the bending direction restriction mechanism, and
   the shape sensor, which is disposed on the bending direction restriction mechanism, is combined such that a direction of possible bending is restricted so as to substantially agree with the direction of easy bending in the bending restriction section, and is combined such that free bending in any direction is possible in the free bending section, wherein at least one set of a detecting unit is disposed in a part of the shape sensor, which corresponds to the free bending section, the detecting unit being composed of two detecting parts such that detection-directivity directions, in which the detection sensitivity is highest, are set at about 90° relative to a direction about the axis of the center line of the bending direction restriction mechanism, and a detection-directivity direction of the detecting part of the shape sensor disposed on the bending restriction section is different from the detection-directivity directions of the two detecting parts of the detecting unit disposed at the free bending section.

2. The bending apparatus of claim 1, wherein the detecting part includes:

a first detecting part configured such that a detection-directivity direction, in which the detection sensitivity is highest, is set to be substantially the same direction as the direction of easy bending of the one-directional bending restriction section in a part corresponding to the one-directional bending restriction section of the bending direction restriction mechanism, and such that the detection-directivity direction is set to be substantially the same direction as the detection-directivity direction, which is set in the bending restriction section, in a part corresponding to the free bending section neighboring the bending restriction section, and a second detecting part configured such that the detection-directivity direction is set in a direction different from the detection-directivity direction of the first detecting part.

3. The bending apparatus of claim 2, wherein an angle, which is formed between the detection-directivity direction of the first detecting part and the detection-directivity direction of the second detecting part, is about 90° relative to a direction about the axis of the center line of the bending direction restriction mechanism.

4. The bending apparatus of claim 1, wherein the detecting part comprises two detecting sections, and the two detecting sections are configured such that detection-directivity directions, in which the detection sensitivity is highest, are set to be substantially the same directions as the two directions of easy bending of the two-directional bending restriction section in a part corresponding to the two-directional bending restriction section of the bending direction restriction mechanism, and such that the detection-directivity directions are set to be substantially the same directions as the detection-directivity directions of the two detecting sections, which are set in the bending restriction section, in a part corresponding to the free bending section neighboring the bending restriction section.

5. The bending apparatus of claim 4, wherein an angle, which is formed between the two directions of easy bending in the two-directional bending restriction section, is about 9020 relative to a direction about the axis of the center line of the bending direction restriction mechanism.

6. The bending apparatus of claim 1, wherein the bending direction restriction mechanism is a part of an endoscope, the one-directional bending restriction section is a coupling structure of annular members configured such that a plurality of annular members are juxtaposed along the direction of the center line of the bending direction restriction mechanism, and a direction of possible bending between a pair of the annular members, which are disposed in a neighboring state along the direction of the center line, is restricted to an up-and-down direction or a left-and-right direction of the endoscope about rotational shafts which are provided to extend in a direction perpendicular to the direction of the center line of the bending direction restriction mechanism, the two-directional bending restriction section is a coupling structure of annular members configured such that rotational shafts for the up-and-down direction and rotational shafts for the left-and-down direction are alternately arranged along the direction of the center line and directions of possible bending are restricted to four directions of the up-and-down directions and left-and-right directions of the endoscope, the free bending section is formed of a flexible tube, and the direction of easy bending of the bending direction restriction mechanism is parallel to the directions of possible bending of the coupling structures of the annular members, which are determined by the rotational shafts of the one-directional bending restriction section and by the rotational shafts for the up-and-down direction and the rotational shafts for the left-and-right direction of the two-directional bending restriction section.

7. The bending apparatus of claim 6, wherein the one-directional bending restriction section is disposed at a position where curvature can be measured, and the plurality of detecting parts of the two-directional bending restriction section and the free bending section are disposed at desired positions where curvature can be measured.

8. The bending apparatus of claim 6, wherein the annular members are configured to directly or indirectly hold at least a part of the shape sensor by a cylindrical holding member disposed on an inner peripheral surface side and configured to hold at least a part of the shape sensor, or a sensor holding recess portion disposed on an outer peripheral surface side and configured to hold at least a part of the shape sensor, or a combination of the cylindrical holding member and the sensor holding recess portion.

9. The bending apparatus of claim 6, wherein at least a part of the shape sensor is held on an outer peripheral surface of a resin-made tube which is built in the endoscope.

10. The bending apparatus of claim 9, wherein the resin-made tube is at least one of a channel tube for insertion of a therapeutic device, a tube for feeding air/water and a tube for feeding jet water, which are built in the endoscope.

11. A bending apparatus comprising:

a shape sensor including a light source, an optical fiber configured to propagate desired detection light which is radiated from the light source, a detecting part disposed at a part of the optical fiber, and a light detector configured to detect the detection light propagated through the optical fiber, the shape sensor being configured to utilize a variation in optical characteristics, which is detected by the detecting part in accordance with a variation of curvature of the optical fiber when the optical fiber is bent, and the shape sensor being freely bendable in any direction and having directivity in detection sensitivity for a bending direction; and a bending direction restriction mechanism which is combined with the shape sensor and has bending directivity including such a property of ease in bending that bending is easy in at least a specific direction other than a direction of a center line, and such a property of difficulty in bending that bending is difficult in directions other than the specific direction, wherein the shape sensor has different directivity of detection sensitivity of the detecting part, relative to a bending direction of the optical fiber, and a detection-directivity direction, in which the detection sensitivity is highest, substantially agrees with a direction of easy bending of the bending direction restriction mechanism in at least a certain range in the direction of the center line of the bending direction restriction mechanism, wherein at least a part of the bending direction restriction mechanism includes a one-directional bending restriction section in which the direction of easy bending is restricted to only one direction relative to a direction about an axis of the center line of the bending direction restriction mechanism, or a two-directional bending restriction section in which the direction of easy bending is restricted to two directions, and a free bending section which is freely bendable in all directions relative to the direction about the axis of the center line of the bending direction restriction mechanism, the shape sensor, which is disposed on the bending direction restriction mechanism, is combined such that a direction of possible bending is restricted so as to substantially agree with the direction of easy bending in the bending restriction section, and is combined such that free bending in any direction is possible in the free bending section, wherein at least one set of a detecting unit is disposed in a part of the shape sensor, which corresponds to the free bending section, the detecting unit being composed of two detecting parts such that detection-directivity directions, in which the detection sensitivity is highest, are set at about 90° relative to a direction about the axis of the center line of the bending direction restriction mechanism, and a detection-directivity direction of the detecting part of the shape sensor disposed on the bending restriction section is different from the detection-directivity directions of the two detecting parts of the detecting unit disposed at the free bending section.

12. The bending apparatus of claim 11, wherein the detecting part includes:

a first detecting part configured such that a detection-directivity direction, in which the detection sensitivity is highest, is set to be substantially the same direction as the direction of easy bending of the one-directional bending restriction section in a part corresponding to the one-directional bending restriction section of the bending direction restriction mechanism, and such that the detection-directivity direction is set to be substantially the same direction as the detection-directivity direction, which is set in the bending restriction section, in a part corresponding to the free bending section neighboring the bending restriction section, and a second detecting part configured such that the detection-directivity direction is set in a direction different from the detection-directivity direction of the first detecting part.

13. The bending apparatus of claim 12, wherein an angle, which is formed between the detection-directivity direction of the first detecting part and the detection-directivity direction of the second detecting part, is about 90° relative to a direction about the axis of the center line of the bending direction restriction mechanism.

14. The bending apparatus of claim 11, wherein the detecting part comprises two detecting sections, and the two detecting sections are configured such that detection-directivity directions, in which the detection sensitivity is highest, are set to be substantially the same directions as the two directions of easy bending of the two-directional bending restriction section in a part corresponding to the two-directional bending restriction section of the bending direction restriction mechanism, and such that the detection-directivity directions are set to be substantially the same directions as the detection-directivity directions of the two detecting sections, which are set in the bending restriction section, in a part corresponding to the free bending section neighboring the bending restriction section.

15. The bending apparatus of claim 14, wherein an angle, which is formed between the two directions of easy bending in the two-directional bending restriction section, is about 90° relative to a direction about the axis of the center line of the bending direction restriction mechanism.

16. The bending apparatus of claim 11, wherein the bending direction restriction mechanism is a part of an endoscope, the one-directional bending restriction section is a coupling structure of annular members configured such that a plurality of annular members are juxtaposed along the direction of the center line of the bending direction restriction mechanism, and a direction of possible bending between a pair of the annular members, which are disposed in a neighboring state along the direction of the center line, is restricted to an up-and-down direction or a left-and-right direction of the endoscope about rotational shafts which are provided to extend in a direction perpendicular to the direction of the center line of the bending direction restriction mechanism, the two-directional bending restriction section is a coupling structure of annular members configured such that rotational shafts for the up-and-down direction and rotational shafts for the left-and-down direction are alternately arranged along the direction of the center line and directions of possible bending are restricted to four directions of the up-and-down directions and left-and-right directions of the endoscope, the free bending section is formed of a flexible tube, and the direction of easy bending of the bending direction restriction mechanism is parallel to the directions of possible bending of the coupling structures of the annular members, which are determined by the rotational shafts of the one-directional bending restriction section and by the rotational shafts for the up-and-down direction and the rotational shafts for the left-and-right direction of the two-directional bending restriction section.

17. The bending apparatus of claim 16, wherein the one-directional bending restriction section is disposed at a position where curvature can be measured, and the plurality of detecting parts of the two-directional bending restriction section and the free bending section are disposed at desired positions where curvature can be measured.

18. The bending apparatus of claim 16, wherein the annular members are configured to directly or indirectly hold at least a part of the shape sensor by a cylindrical holding member disposed on an inner peripheral surface side and configured to hold at least a part of the shape sensor, or a sensor holding recess portion disposed on an outer peripheral surface side and configured to hold at least a part of the shape sensor, or a combination of the cylindrical holding member and the sensor holding recess portion.

19. The bending apparatus of claim 16, wherein at least a part of the shape sensor is held on an outer peripheral surface of a resin-made tube which is built in the endoscope.

20. The bending apparatus of claim 19, wherein the resin-made tube is at least one of a channel tube for insertion of a therapeutic device, a tube for feeding air/water and a tube for feeding jet water, which are built in the endoscope.

* * * * *